United States Patent
Ruhge et al.

(10) Patent No.: US 9,513,117 B2
(45) Date of Patent: Dec. 6, 2016

(54) SITU BLADE MOUNTED TIP GAP MEASUREMENT FOR TURBINES

(71) Applicants: Forrest R. Ruhge, Orlando, FL (US); Clifford Hatcher, Jr., Orlando, FL (US)

(72) Inventors: Forrest R. Ruhge, Orlando, FL (US); Clifford Hatcher, Jr., Orlando, FL (US)

(73) Assignee: Siemens Energy, Inc., Orlando, FL (US)

( * ) Notice: Subject to any disclaimer, the term of this patent is extended or adjusted under 35 U.S.C. 154(b) by 128 days.

(21) Appl. No.: 14/043,913

(22) Filed: Oct. 2, 2013

(65) Prior Publication Data

US 2015/0090882 A1    Apr. 2, 2015

(51) Int. Cl.
| | |
|---|---|
| *G01B 21/16* | (2006.01) |
| *G01B 11/14* | (2006.01) |
| *G01M 15/02* | (2006.01) |
| *G01N 21/88* | (2006.01) |
| *F01D 21/00* | (2006.01) |

(52) U.S. Cl.
CPC .............. *G01B 21/16* (2013.01); *F01D 21/003* (2013.01); *G01B 11/14* (2013.01); *G01M 15/02* (2013.01); *G01N 21/8803* (2013.01); *F05D 2270/80* (2013.01); *F05D 2270/821* (2013.01)

(58) Field of Classification Search
CPC ........ G01B 21/16; G01B 11/14; G01M 15/02; G01M 15/14; G01M 13/028; G01M 13/045
USPC ............................ 73/660, 659, 655, 657, 661
See application file for complete search history.

(56) References Cited

U.S. PATENT DOCUMENTS

| | | | |
|---|---|---|---|
| 4,322,887 A | | 4/1982 | Burton |
| 4,395,827 A | * | 8/1983 | Stowe ..................... F01D 11/08 33/613 |
| 4,518,917 A | | 5/1985 | Oates et al. |
| (Continued) | | | |

FOREIGN PATENT DOCUMENTS

| | | |
|---|---|---|
| DE | 1919945 A1 | 4/1971 |
| DE | 002730508 | 1/1979 |
| (Continued) | | |

OTHER PUBLICATIONS

Bluetooth Accessory Pack BAP1.0, Philtec E-Newsletter, Dec. 9, 2012, www.philtec.com.
(Continued)

*Primary Examiner* — Michael A Lyons
*Assistant Examiner* — Suman K Nath

(57) ABSTRACT

Turbine blade tip clearance is measured in a fully assembled turbine casing by mounting a contact or non-contact displacement probe on a turbine blade that generates data indicative of probe distance from the turbine casing that circumferentially surrounds the blade. Variations in probe distance data are recorded as the blade circumferentially sweeps the turbine casing when the turbine is operated in turning gear mode. Blade rotational position data are collected by a rotational position sensor. A data processing system correlates the distance and rotational position data with localized blade tip gap at angular positions about the turbine casing circumference. An optical camera inspection system may be coupled to a turbine blade to obtain visual inspection information within the turbine casing. This method and apparatus provide an accurate and cost effective solution for accessing turbine casing deformation impact on blade tip clearance and rotor/casing alignment.

19 Claims, 9 Drawing Sheets

(56) References Cited

U.S. PATENT DOCUMENTS

| | | |
|---|---|---|
| 4,632,352 A | 12/1986 | Stoll |
| 4,704,906 A * | 11/1987 | Churchill et al. ............... 73/660 |
| 4,911,004 A | 3/1990 | Leon |
| 4,987,555 A | 1/1991 | Twerdochlib |
| 5,670,879 A | 9/1997 | Zombo et al. |
| 6,575,011 B1 | 6/2003 | Busby et al. |
| 6,848,193 B1 | 2/2005 | Kirzhner |
| 7,579,844 B2 | 8/2009 | Ducheminsky et al. |
| 8,102,539 B2 | 1/2012 | Ghulam |
| 8,138,753 B2 | 3/2012 | Eberl et al. |
| 8,174,931 B2 | 5/2012 | Vartanian et al. |
| 8,482,302 B2 | 7/2013 | Suckling et al. |
| 8,485,038 B2 * | 7/2013 | Sengupta ............... F01D 21/003 382/103 |
| 8,684,669 B2 | 4/2014 | Chehab et al. |
| 2003/0020496 A1 | 1/2003 | Eyraud et al. |
| 2003/0222640 A1 | 12/2003 | Twerdochlib et al. |
| 2005/0088271 A1* | 4/2005 | Lau ........................ G01R 31/07 337/206 |
| 2008/0190211 A1 | 8/2008 | Secq |
| 2008/0218181 A1 | 9/2008 | Ducheminsky et al. |
| 2009/0000101 A1 | 1/2009 | Reynolds et al. |
| 2009/0165540 A1 | 7/2009 | Craig |
| 2009/0289620 A1* | 11/2009 | Suckling ............... F01D 21/003 324/207.16 |
| 2010/0046008 A1* | 2/2010 | Ghulam ................. G01B 11/24 356/614 |
| 2010/0117859 A1 | 5/2010 | Mitchell et al. |
| 2013/0167392 A1 | 7/2013 | Boyer et al. |
| 2013/0312249 A1* | 11/2013 | Buchal ................... F01D 11/14 29/593 |

FOREIGN PATENT DOCUMENTS

| | | |
|---|---|---|
| EP | 0242107 A2 | 10/1987 |
| EP | 2397656 A1 | 12/2011 |
| GB | 2112080 A | 7/1983 |
| GB | 2460248 | 11/2009 |
| GB | 2462829 | 2/2010 |
| JP | S61161407 A | 1/1988 |

OTHER PUBLICATIONS

RPI-1031 for a surface mount type 4 direction detector, Appendix 1-Rev 2.0, copyright 2008, published by ROHM Co. Ltd., Kyoto, Japan.

Analog Devices Programmable 360° Inclinometer ADIS16203, publication No. DO6108-0-1/10(A), Copyright 2006-2010, by Analog Devices Inc. of Norwood, Massachusetts.

* cited by examiner

SITU BLADE MOUNTED TIP GAP MEASUREMENT FOR TURBINES

CROSS-REFERENCE TO RELATED APPLICATIONS

This application claims the benefit of co-pending, commonly owned at time of filing, U.S. utility patent application entitled "TURBINE BLADE-MOUNTED SENSOR FIXTURE FOR TIP GAP MEASUREMENT", filed herewith, on Oct. 2, 2013 and assigned Ser. No. 14/043,878, which is incorporated by reference herein.

BACKGROUND OF THE INVENTION

1. Field of the Invention

The invention relates to in-situ measurement of steam or gas turbine blade tip gap between rotating blades and the circumscribing turbine casing ring segment. More particularly, embodiments of the invention relate to in-situ blade tip gap measurement by mounting a radially oriented displacement sensor directly on a turbine blade while in-situ within an industrial gas turbine and rotating the rotor so that the blade sweeps at least a portion of the circumscribing turbine casing ring segment in either the compressor or hot gas turbine sections. In other embodiments of the invention the entire circumference of the circumscribing casing ring segment is swept by rotating the rotor while the industrial gas turbine is operated in turning gear mode.

2. Description of the Prior Art

During assembly and at periodic times throughout the life of a gas turbine blade tip clearances must be measured. Proper tip clearance enables better efficacy of gas turbines and lowers harmful emissions. To date there are ways of measuring tip clearances, but the methods requiring the removal of the upper casing that circumscribes the turbine blade tips during measurement, limited number of inspection points, or take a relatively long time to complete.

There are typically two known common methods for measuring blade tip clearances. In the first method the measurement of tip clearance is typically accomplished b y removing the turbine or compressor case upper half to provide access to the blades. Shims are then inserted between the blades tips and the flow path side or ring segments of the lower case at the horizontal joint. Measurements are typically taken at the leading and trailing edge sides of the blade tips for every blade. These measurements are referred to as half shell measurements. This method provides very little accuracy or reproducibility because the lower case tends to change shape without the upper case in place. Also, the half shell measurement locations are not necessarily representative of the local case shape at all angular rotational positions about the entire rotational surface swept by the turbine blade.

The second known common method for measuring blade tip clearances is by opening an inspection port in the side of the engine that is aligned with the blade path. A contact or non-contact probe is inserted into the port to measure the distance of the blade tip from the gas path side of the case or ring segments. There are a limited number of these inspection ports oriented about the turbine casing. Therefore only data from select rows and cord positions can be obtained. Furthermore, as noted above in the description of the first known inspection method the inspection locations may not be representative of the casing shape about the entire rotational circumference of the turbine. In some spots, due to casing shape disparities, there may be varying tip gap.

Thus, a need exists for a method to measure turbine blade tip clearances in-situ within an assembled turbine without removing part of the turbine casing that circumscribes the blade tips.

A need also exists for a method to measure turbine blade tip clearances in-situ within an assembled turbine casing, so that localized blade tip gap differences can be identified and measured.

An additional need exists for a method to determine whether the turbine rotor assembly is aligned within its circumscribing turbine casing, so that alignment can be adjusted to assure rotor rotational axis concentricity within the casing. For example, so that turbine vane carriers are centered to the rotor during alignment verification.

Another need exists for a method to inspect the interior of the assembled turbine casing visually about the entire blade rotational circumference.

SUMMARY OF THE INVENTION

Accordingly, an object of the invention is to measure turbine blade tip clearances in-situ within an assembled turbine without removing part of the turbine casing that circumscribes the blade tips.

It is also an object of the invention to measure turbine blade tip clearances in-situ within an assembled turbine casing, so that localized blade tip gap differences can be identified and measured.

An additional object of the invention is to determine whether the turbine rotor assembly is aligned within its circumscribing turbine casing, so that alignment can be adjusted to assure rotor rotational axis concentricity within the casing, including but not limited to turbine vane carriers/rotor centering during alignment verification.

Another object of the invention is to inspect the interior of the assembled turbine casing visually about the entire blade rotational circumference.

These and other objects are achieved in accordance with embodiments of the present invention by using the blade (not the case) as the reference measurement location without removing the cover as is traditionally done. This enables the measurement of the tip clearance of a particular blade along the entire path it makes during one or more revolutions in the engine on turning gear. Embodiments of this method of tip clearance measurement include a contact or non-contact displacement sensor coupled with a data acquisition system to record the measured displacement between the blade and the corresponding circumscribing turbine casing (e.g., the gas path side of the case or the ring segments). In some embodiments an optical camera is mounted on a blade to capture images within the turbine case during blade rotation. In addition, a digital inclinometer or gyroscope is used to relate each measurement to a an angular rotational clock position around the rotor by measuring the blade orientation with respect to gravitational pull or a reference position. Alternatively angular position can be determined by a sensor that monitors the rotor rotational position or any other sensor location that is coupled to the turbine. The gap measurement system is delivered to the blade location by a flexible snake arm delivered from the inlet or exhaust of the unit or through an existing inspection port. The gap measurement displacement and data acquisition system are coupled to the specified blade using a mechanical, magnetic, or adhesive gripping mechanism. The delivery snake arm is removed and the system logs displacement and rotational data as the rotor rotates. To retrieve the data acquisition system the arm is again inserted to deactivate the griping mechanism and retrieve the data acquisition system. Data collected can be either stored the data acquisition system internal storage, removable media, or can be streamed wirelessly in real time during measurement. Data collected can also be communicated via a direct cable connection. This method and apparatus provide an accurate and cost effective solution for accessing turbine casing deformation impact on blade tip clearance and rotor/casing alignment.

More particularly, embodiments of the invention feature a method for measuring gas turbine blade tip and turbine casing radial clearance gap. The method is performed on a gas turbine with a rotatable rotor having a turbine blade with a radially outwardly projecting tip in opposed spaced relationship with a circumscribing turbine casing, defining a gap there between. At least one displacement sensor that is capable of generating data set of displacement relative to the circumscribing turbine casing is coupled to the turbine blade. A rotor rotational position sensor is coupled to the turbine. The rotor is rotated so that the turbine blade tip sweeps at least a portion of the circumscribing turbine casing while generating the displacement data set with the displacement sensor and a rotational position data set with rotational position sensor. The displacement and rotational position data sets are acquired with a data acquisition system that is coupled to the displacement and rotational position sensors. A data analyzer system is coupled to the data acquisition system and is used to correlate blade tip and circumscribing turbine casing radial clearance gap relative to rotational position with the displacement and rotational data sets.

Other embodiments of the invention feature a method for measuring gas turbine blade tip and turbine casing radial clearance gap in a gas turbine with a rotatable rotor having a turbine blade with a radially outwardly projecting tip in opposed spaced relationship with a circumscribing turbine casing, defining a gap there between. At least one infra-red displacement sensor that is capable of generating data set of displacement relative to the circumscribing turbine casing to the turbine blade is coupled to the turbine blade, as is a tilt sensor that is capable of generating a data set of blade rotational position. The rotor is rotated so that the turbine blade tip sweeps at least a portion of the circumscribing turbine casing while generating the displacement data set with the displacement sensor and a rotational position data set with tilt sensor. The displacement and rotational position data sets are acquired with a data acquisition system that is coupled to the turbine blade as well as the displacement and tilt sensors. A data analyzer that is coupled to the data acquisition system by a wireless communication system correlates blade tip and circumscribing turbine casing radial clearance gap relative to rotational position with the displacement and rotational data sets.

Additional embodiments of the invention feature a system for measuring gas turbine blade tip and turbine casing radial clearance gap in a gas turbine having a rotatable rotor, a turbine blade coupled to the rotor with a radially outwardly projecting tip in opposed spaced relationship with a circumscribing turbine casing, defining a gap there between. The system comprises at least one displacement sensor that is capable of generating data set of displacement relative to the circumscribing turbine casing, coupled to the turbine blade. A rotor rotational position sensor that is capable of generating a data set of blade rotational position is coupled to the turbine. A data acquisition system is coupled to the displacement and rotational position sensors, for acquiring the displacement and rotational position data sets during rotor rotation as the turbine blade tip sweeps at least a portion of the circumscribing turbine casing. A data analyzer system is coupled to the data acquisition system, for correlating with the displacement and rotational data sets the blade tip and circumscribing turbine casing radial clearance gap relative to rotational position.

The objects and features of the present invention may be applied jointly or severally in any combination or subcombination by those skilled in the art.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
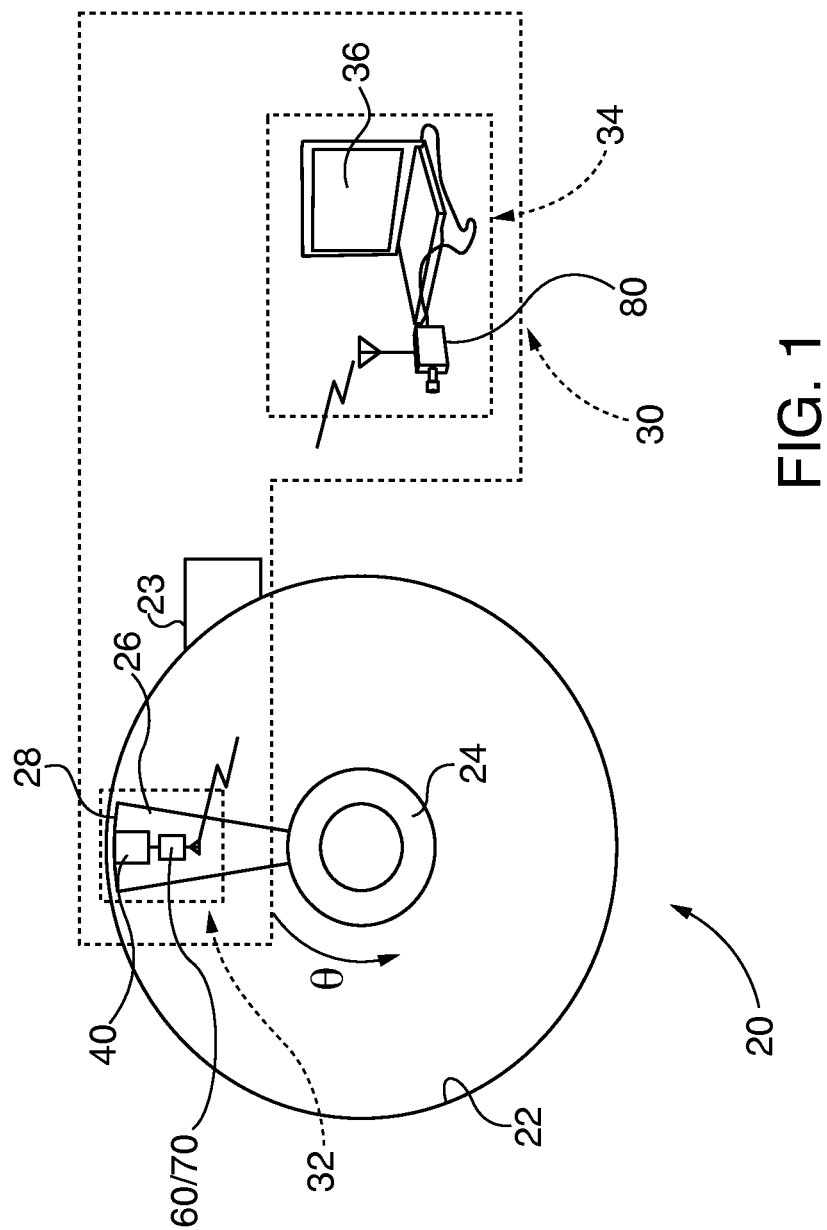
FIG. 1 is an elevational schematic view of an embodiment of a turbine tip gap clearance measurement system of the invention coupled to a turbine, including a blade mounted instrument system with a probe system and a data acquisition system that are communicatively coupled to a data processing system outside the turbine via a wireless communication system.

After considering the following description, those skilled in the art will clearly realize that the teachings of the invention can be readily utilized in methods and apparatus for in-situ measurement of steam or gas turbine blade tip gap between rotating blades and the circumscribing turbine casing (e.g., the ring segments or gas paths defined within the casing), using the blade (not the case) as the reference measurement location without removing the cover as is traditionally done. This enables the measurement of the tip clearance of a particular blade along the entire path it makes during one or more revolutions in the engine on turning gear. The measurement system can be moved from blade to blade so that tip gap information can be obtained for a plurality of or all of the blades about their full 360 degree rotational sweep, including critical measurements at the six o-clock or bottom casing location that is susceptible to transient and permanent thermal distortion during engine operation. By performing the tip gap measurements on a fully assembled turbine casing the gathered information is indicative of the actual clearances experienced by an operational turbine, including any potential mechanical or thermal distortions imparted on the casing structure after its assembly. Also, after sufficient cool down of an in-service engine, pre-rebuild tip gap measurements can be obtained for service diagnostic evaluation and to obtain pre-rebuild baseline clearance information suitable for "before" and "after" rebuild evaluation and documentation.

Embodiments of this method of tip clearance measurement and the measurement system include a contact or non-contact displacement sensor coupled with a data acquisition system to record the measured displacement between the blade and the corresponding circumscribing turbine casing (e.g., the gas path side of the case or the ring segments). In some embodiments an optical camera is mounted on a blade to capture images within the turbine case during blade rotation. In addition, a digital inclinometer or gyroscope is used to relate each measurement to a an angular rotational clock position around the rotor by measuring the blade orientation with respect to gravitational pull or a reference position. Alternatively angular position can be determined by a sensor that monitors the rotor rotational position or any other sensor location that is coupled to the turbine. The gap measurement system is delivered to the blade location by a flexible snake arm delivered from the inlet or exhaust of the unit or through an existing inspection port. The gap measurement displacement and data acquisition system are coupled to the specified blade using a mechanical, magnetic, or adhesive gripping mechanism. The delivery snake arm is removed and the system logs displacement and rotational data as the rotor rotates. To retrieve the data acquisition system the arm is again inserted to deactivate the griping mechanism and retrieve the data acquisition system. Data collected can be either stored the data acquisition system internal storage, removable media, or can be streamed wirelessly in real time during measurement. Data collected can also be communicated via a direct cable connection. A data analyzer coupled to the data acquisition system correlates blade tip and circumscribing turbine casing radial clearance gap relative to rotational position with the displacement and rotational data sets. This method and apparatus provide an accurate and cost effective solution for accessing turbine casing deformation impact on blade tip clearance and rotor/casing alignment.

Figure 2:
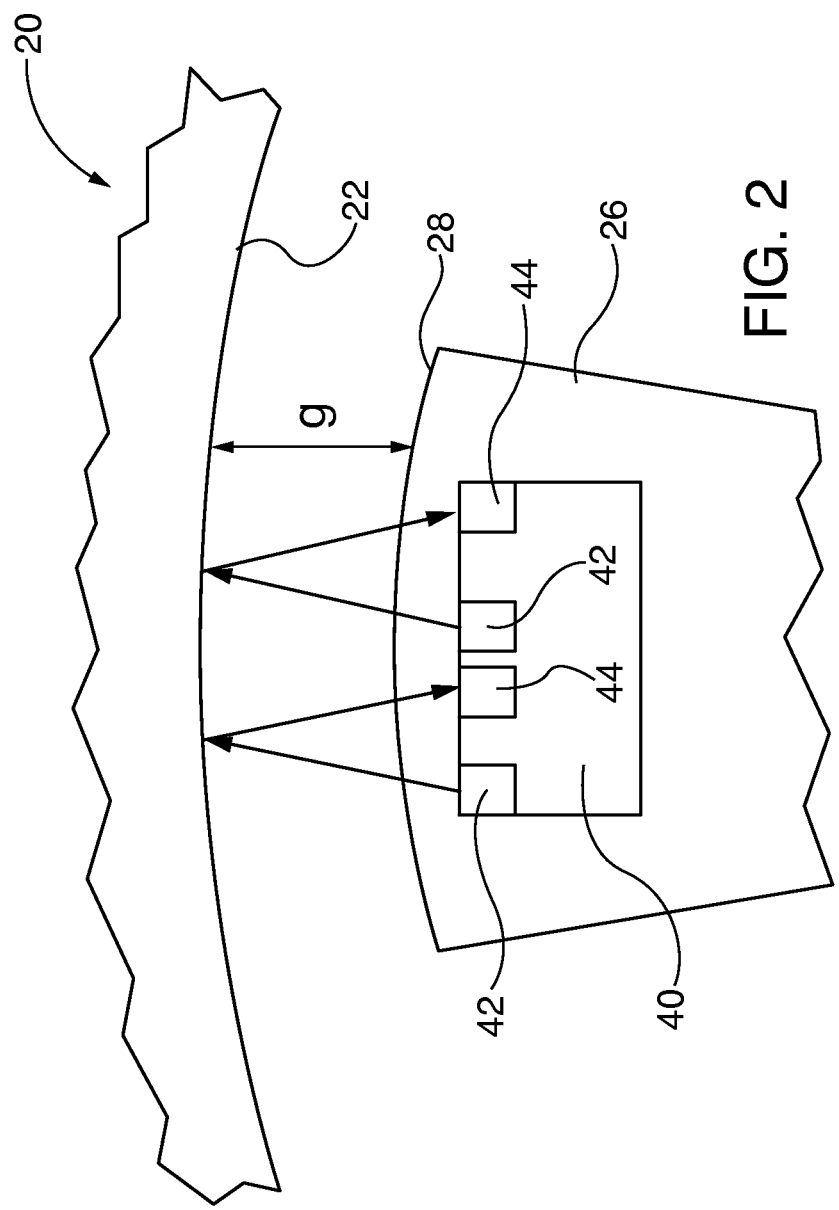
FIG. 2 is a detailed schematic view of an embodiment of a probe system, including displacement sensors, coupled to a turbine blade.

FIGS. 1 and 2 show schematically a gas turbine 20, with a turbine casing having an inner circumferential ring segment 22 that defines an inner diameter and an access port 23. Rotor 24 rotates within the turbine 20. Affixed to the rotor 24 are a plurality of rows of turbine blades 26 that are designated $B_1$-$B_N$. Only a single blade row is schematically shown in FIG. 1. As a blade 26 rotates with the rotor 24, it defines a rotational displacement θ; its blade tip 28 sweeps the circumscribing inner circumferential ring segment 22. Radial separation between the mutually opposed and spaced blade tip 28 and the ring segment 22 inner diameter is designated by gap g.

The blade tip clearance system 30 embodiment shown in FIGS. 1 and 2 comprises a blade mounted instrument 32 that is communicatively coupled to a blade tip clearance data analyzer system 34. In this embodiment communication is established via wireless communication system, for example one utilizing Bluetooth communications protocol. The data analyzer system 34 may be incorporated into a personal computer 36. Details of the blade clearance system 30 architecture and function are further described.

Figure 8:
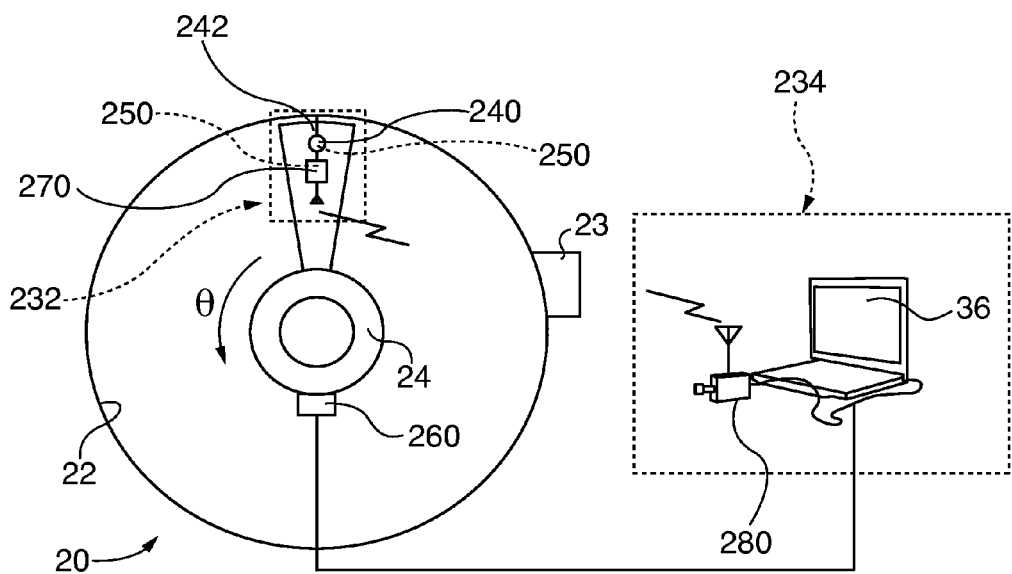
FIGS. 8 and 9 are elevational schematic view of an embodiment of a turbine tip gap clearance measurement system of the invention coupled to a turbine, including a blade mounted instrument system with a contact displacement probe system and a data acquisition system that are communicatively coupled to a data processing system outside the turbine via a wireless communication system.

The blade mounted instrument 32 includes a displacement probe system 40, which as shown in FIGS. 1 and 2 is a non-contact type displacement probe having at least one photonic energy transmitter 42 and a corresponding receiver 44 of known construction. FIG. 2 shows a probe 40 having an arrayed pair of transmitters and receivers. In this embodiment the transmitted and received photonic energy is in the infra-red spectrum. Alternatively, visible light or ultrasonic non-contact displacement probes or mechanical displacement measurement displacement probes may be substituted for the non-contact probe 40 that is shown in FIG. 1. The displacement probe 40 generates a displacement data set of relative distance between the probe and the circumscribing turbine casing circumferential ring 22. A rotor rotational position acquisition system sensor 60 is also coupled to the blade 26 in order to sense the rotor/corresponding blade's rotational position θ and generate a rotational position data set. The rotational position sensor 60 is of known construction, exemplary embodiments of which may include known tilt, gyroscopic or localized triangulated GPS-type sensors. Alternatively the rotational position sensor function may be performed by an existing turbine rotor 24 rotational position sensor 260 as shown in FIG. 8.

The blade mounted displacement probe system 40 and the rotor/blade rotational system sensor 60 are coupled to data acquisition module 70 that acquires the displacement and rotational position data sets. While the data acquisition module 70 is shown coupled to the turbine blade 26 and receives both the displacement and rotational position data sets, alternative locations and data feed configurations are possible in other embodiments. For example, the sensors 40 and 60 may be coupled jointly or severally to a wireless communication module that in turn communicates with a non-blade mounted data acquisition module. Similarly the data acquisition module function may be divided into separate components that receive separate positional or displacement data sets from the respective sensors 40 and 60.

The data acquisition module 70 sends the displacement and rotational position data sets to the data analyzer system 34 via wireless Bluetooth communication with the data analyzer system interface 80. The data analyzer system 34 includes the data analyzer interface 80 and the personal computer 36; the latter correlates blade tip and circumscribing turbine casing radial clearance gap relative to rotational position with the displacement and rotational data sets received from the data acquisition module 70. Blade tip gap g information and relative rotational position in the data analyzer system 34 is available for further analysis, including by way of example relative concentric alignment of the rotor, rotor blades, turbine vanes and the turbine casing inner diameter, concentricity of the turbine casing itself and identification of potential localized wear patterns within the turbine casing lining. If multiple displacement probes 40 are utilized across the axial length of the blade tip 28 annular patterns, rather than just circular patterns of blade tip gap g about the turbine casing circumference can be acquired and analyzed.

Figure 3:
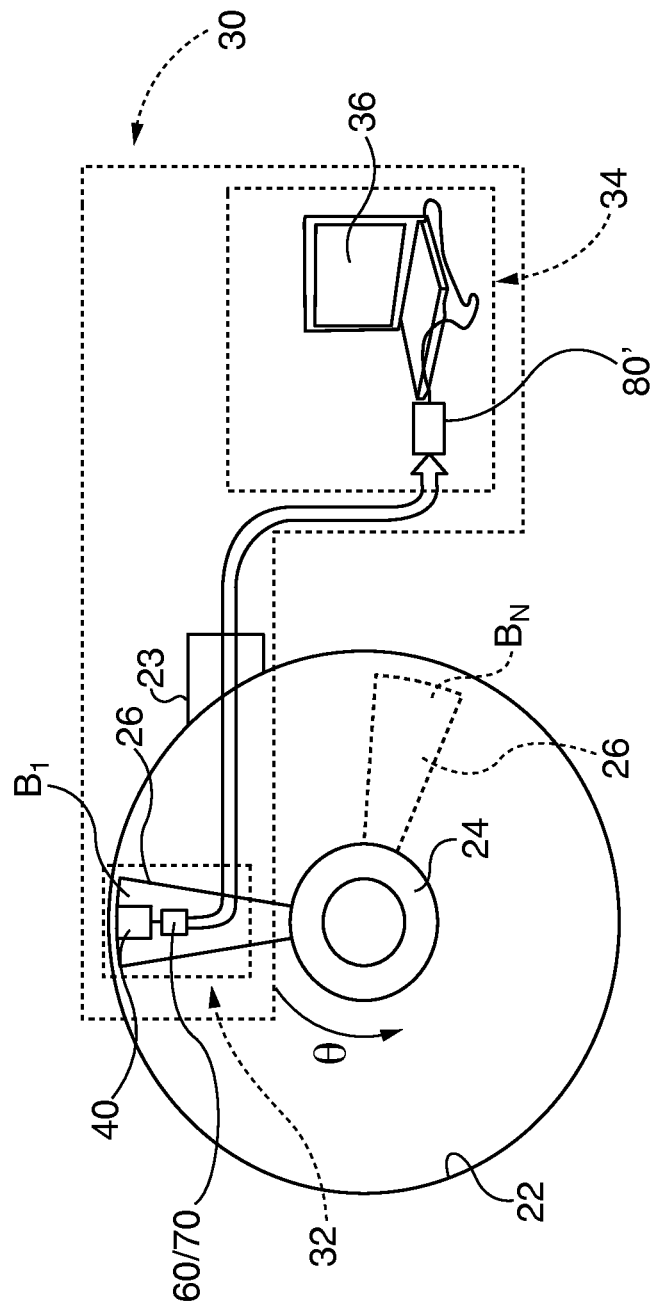
FIG. 3 is an elevational schematic view of another embodiment of a turbine tip gap clearance measurement system of the invention coupled to a turbine, including a blade mounted instrument system with a probe system and a data acquisition system that are communicatively coupled to a data processing system outside the turbine via a portable data storage device transferred from the blade mounted instrument system to a data processing system interface for downloading to the data processing system personal computer.
Figure 4:
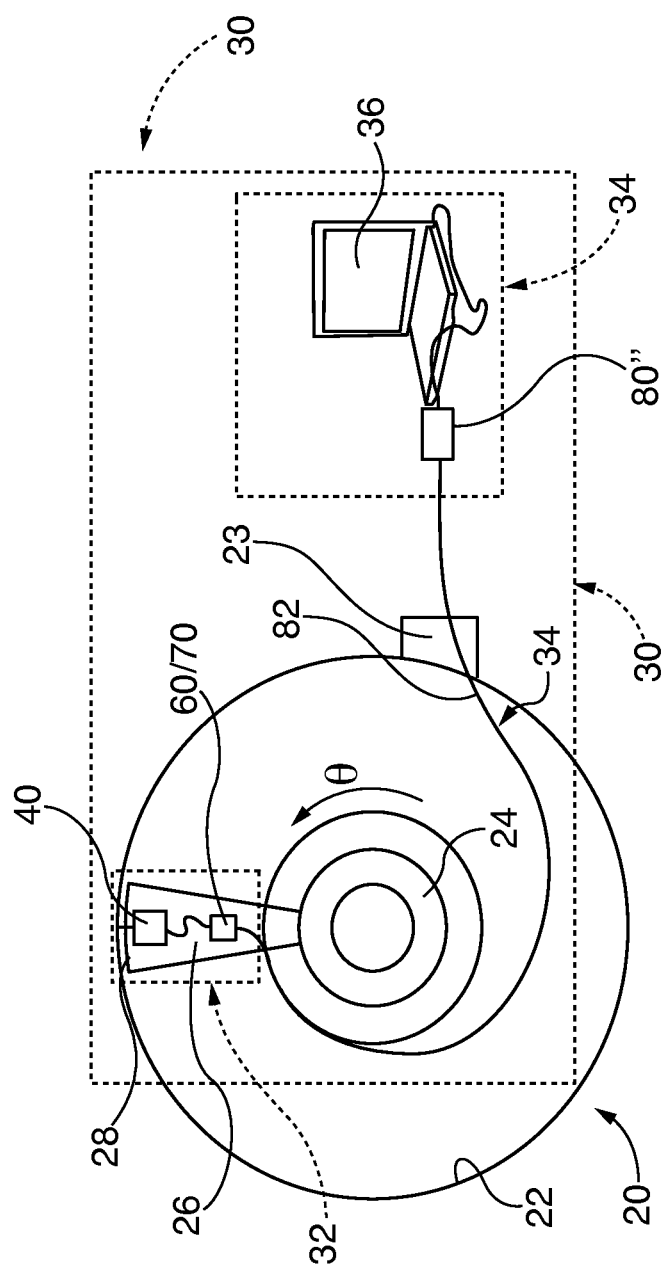
FIG. 4 is an elevational schematic view of another embodiment of a turbine tip gap clearance measurement system of the invention coupled to a turbine, including a blade mounted instrument system with a probe system and a data acquisition system that are communicatively coupled to a data processing system outside the turbine via a cable.

As shown in FIG. 3 by the double arrow the blade mounted instruments 32 can be installed and removed via a turbine access port 23 or manway, or by removing a section of the turbine external housing that does not circumscribe the blade tips 28. Similarly, if a wireless communication system is not utilized between the data acquisition module 70 and the data analyzer system 34, a portable memory device may be incorporated into the data acquisition module and to store the acquired rotational and/or displacement data sets. The memory device is removed after data acquisition by the blade tip clearance system 30 and subsequently transported as shown schematically by the double lines for coupling to the data analyzer interface 80' and for subsequent downloading of the data sets. Alternatively, as shown in FIG. 4, the data acquisition module 70 may be communicatively coupled to the data analyzer interface 80" by a physical cable 82 routed through an access port 23. The cable 82 has sufficient length to be wrapped around the turbine rotor 24.

Figure 6:
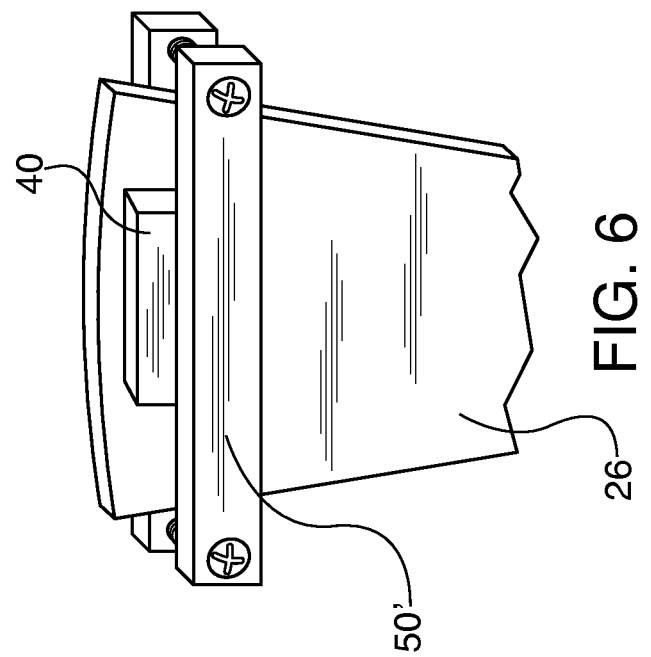
FIG. 6 is a detailed elevational schematic view of an embodiment of a retaining clamp for mounting a probe system of the invention to a turbine blade, having opposed plates that are compressively coupled to a turbine blade circumference by screws.
Figure 5:
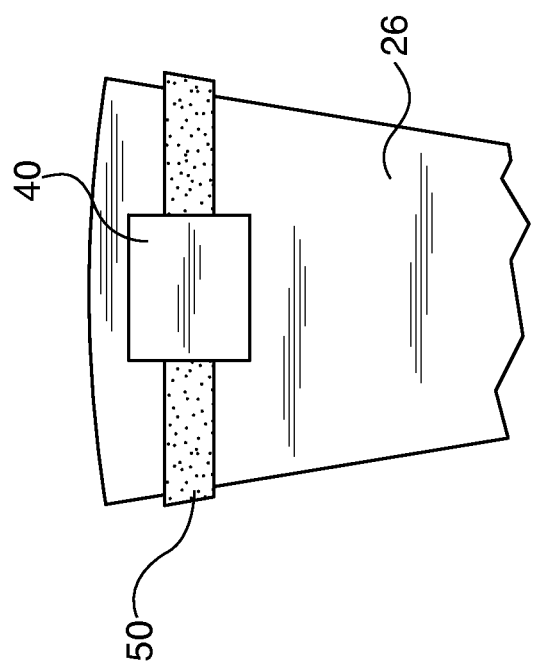
FIG. 5 is a detailed elevational schematic view of an embodiment of a retaining strap for mounting a probe system of the invention to a turbine blade, having mating hook and loop fasteners.

As previously noted the blade mounted instruments 32 are coupled or otherwise affixed to the blade 26 so that they do not inadvertently drop within the turbine interior during a blade gap measurement procedure. As shown in FIG. 5, a probe 40 of the blade mounted instrument is coupled to the blade 26 by a hook and loop fastened strap 50 that is circumferentially wrapped about the blade. In FIG. 6 the probe 40 is coupled to the blade 26 by a retaining clamp 50', having opposed plates that are compressively coupled to a turbine blade circumference by screws.

Figure 7:
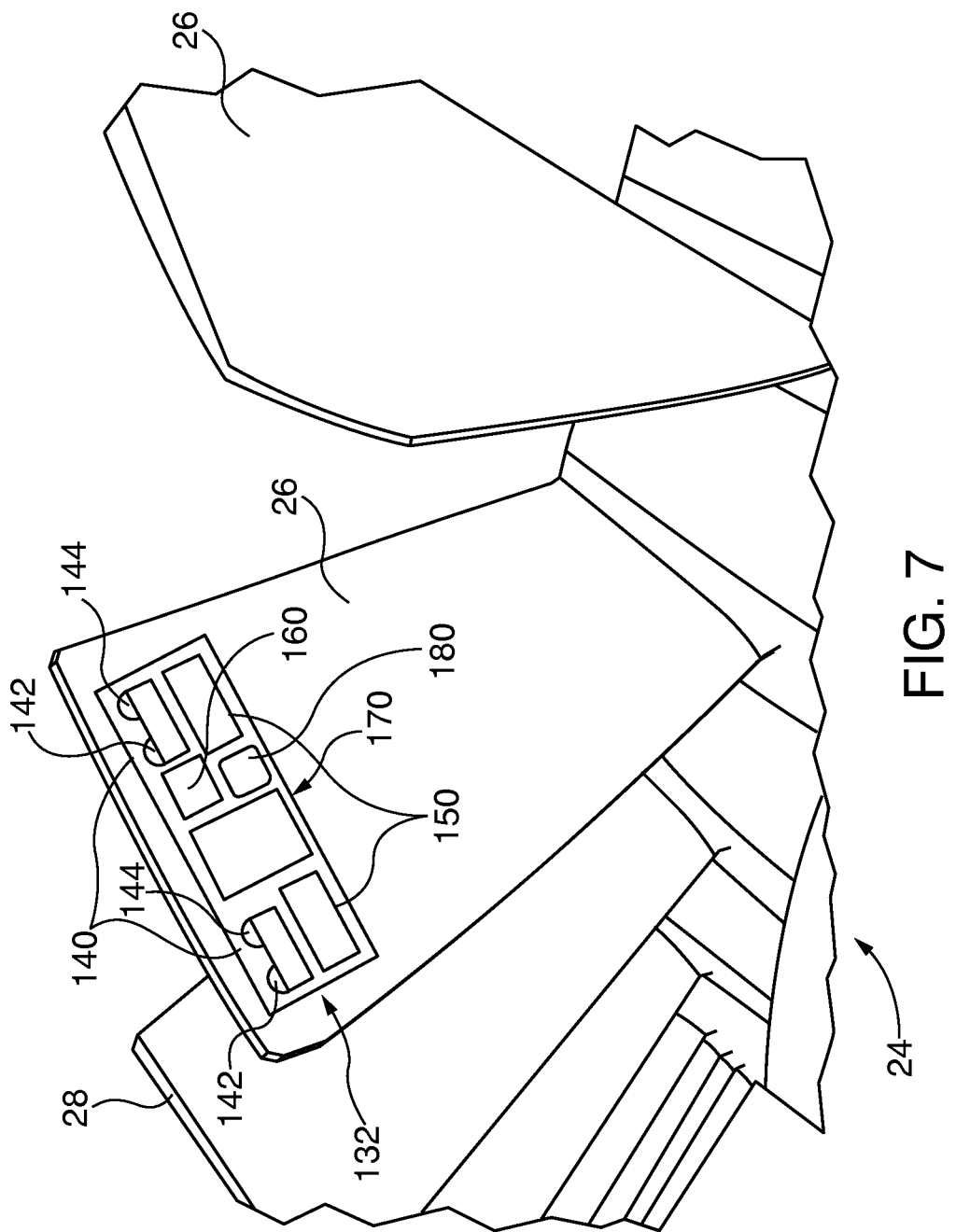
FIG. 7 is a perspective elevational view of an embodiment of a blade mounted instrument that is magnetically coupled to a turbine blade.

FIG. 7 shows an alternative embodiment of a blade tip clearance system blade mounted instrument 132 that is advantageously a printed circuit board upon which are mounted a pair of non-contact, infra-red spectrum photonic displacement probes 142 that are oriented on opposite lateral ends of the blade for generation of displacement data sets. Each of the probes 142 has an infra-red transmitter 142 and an infra-red receiver of known construction. Magnets 150 on opposite sides of the blade mounted instrument 132 couple the instrument to the blade 26 in a fixed position. A tilt sensor 160 generates the rotational positional data set. Data acquisition module 170 is coupled to the displacement probes 140 and the tilt sensor 160 for acquiring the displacement and rotational position data sets and communicating them to the previously described data analyzer system 34 via wireless communication or via physical transfer of a data storage device. Battery 180 powers the blade mounted instrument 132.

Figure 9:
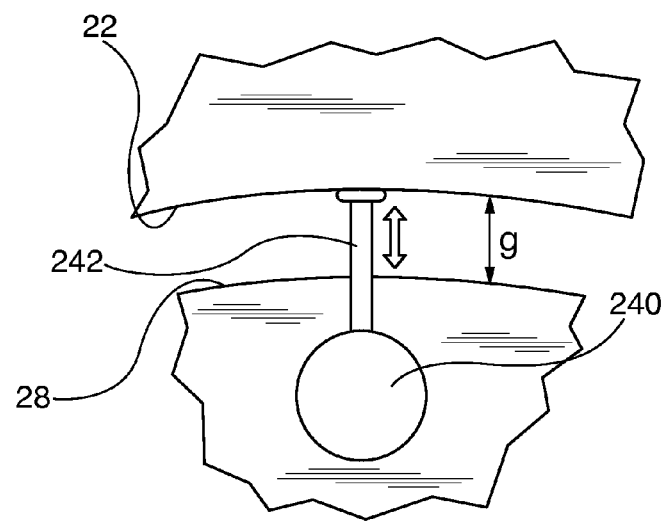

The blade mounted instrument 232 of FIGS. 8 and 9 comprise a contact displacement probe 240 with a displaceable probe tip 242 that is in contact with the blade circumscribing turbine casing inner diameter surface 22. Physical displacement of probe tip 242, as shown by the double-ended arrow, generates a displacement data set. The blade mounted instrument 232 is coupled to blade 26 by one or more magnets 250.

Displacement data generated by the contact displacement probe 240 is gathered by data acquisition module 270 that in turn routes the displacement data to the data analyzer system interface 280 via wireless communication (e.g., Bluetooth) protocols, as previously described. The turbine blade rotational positional data set is generated by the turbine rotor positional sensor 260 rather than a blade-mounted positional sensor. The rotational positional data set is routed to the data analyzer system 234 by known means, such as a communications cable. The data analyzer system 234 correlates the received displacement and rotational position data sets with blade gap about the turbine casing inner diameter 22 as previously described.

Figure 10:
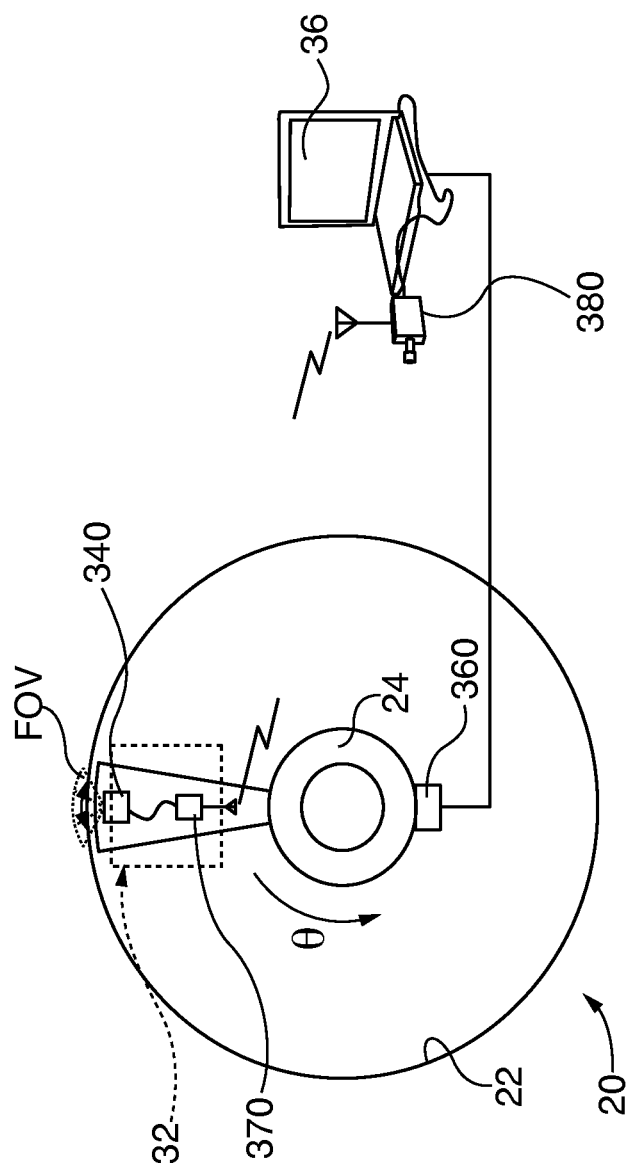
FIGS. 10 and 11 are elevational schematic views of an embodiment of a turbine tip gap clearance measurement system of the invention coupled to a turbine, including a blade mounted instrument system with a probe system, an optical camera inspection system, and a data acquisition system that are communicatively coupled to a data processing system outside the turbine via a wireless communication system.
Figure 11:
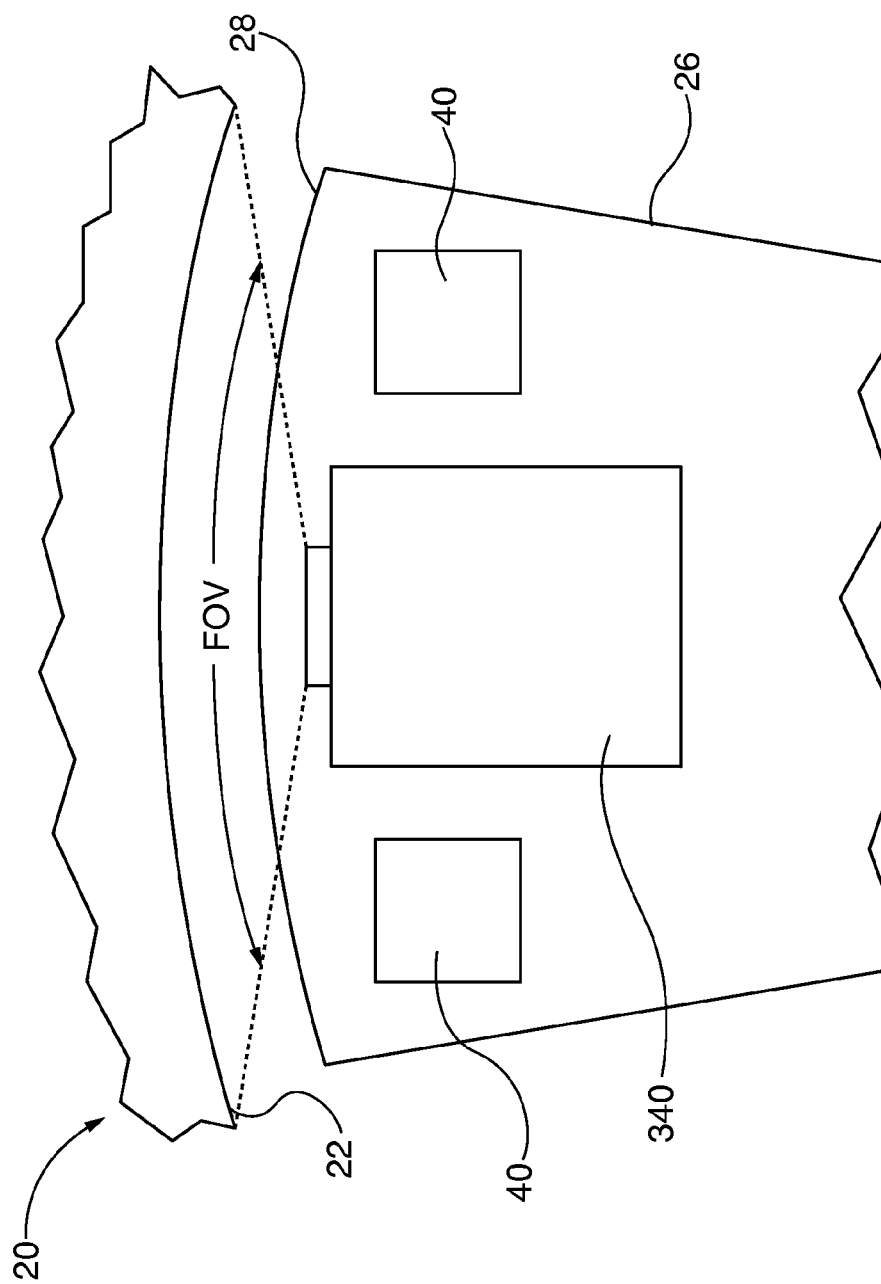

In FIGS. 10 and 11 a blade mounted optical inspection system including an optical camera 340 is coupled to a blade 26 for generating and capturing images within its field of view (FOV) within the turbine 20. The blade mounted data acquisition system 370 acquires the camera image information and routes it to the data analyzer system interface 380 via wireless communication while the rotor rotational position sensor 360 sends a rotational position data set to the data analyzer system computer 36. The optical inspection system camera 340 may capture images within a desired spectral bandwidth (e.g., visible, infra-red, etc.) and may be utilized jointly with or separately from a blade gap measurement system.

Although various embodiments that incorporate the teachings of the present invention have been shown and described in detail herein, those skilled in the art can readily devise many other varied embodiments that still incorporate these teachings. The invention is not limited in its application to the exemplary embodiment details of construction and the arrangement of components set forth in the description or illustrated in the drawings. The invention is capable of other embodiments and of being practiced or of being carried out in various ways. Also, it is to be understood that the phraseology and terminology used herein is for the purpose of description and should not be regarded as limiting. The use of "including;" "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

What is claimed is:

1. A method for measuring gas turbine blade tip and turbine ring segment radial clearance gap, comprising:
    providing a gas turbine including: a turbine casing having an inner circumferential ring segment that fully circumscribes a rotatable rotor oriented within the casing, the rotor having a row of turbine blades radially aligned with the ring segment, each blade having an airfoil that defines an airfoil outer surface and a radially outwardly projecting tip in opposed, spaced relationship with the circumscribing ring segment, each respective blade tip defining a radial clearance gap between itself and the circumscribing ring segment at a plurality of rotational angular positions of the blade and rotor;
    coupling on an airfoil surface of a first one of said blades at least one non-contact displacement sensor that generates a displacement data set of distance between the displacement sensor and the ring segment;

coupling on the airfoil surface of the same first one of said blades a rotor rotational position sensor that generates a rotational position data set indicative of rotational angular orientation of said first blade relative to the circumscribing ring segment;

rotating the rotor so that the blade tip of said first blade sweeps at least a portion of the circumscribing ring segment, while generating the displacement data set with the displacement sensor and a rotational position data set with the rotor rotational position sensor at plural angular positions along the blade tip sweep;

acquiring the displacement and rotational position data sets with a data acquisition system that is coupled to the displacement and rotational position sensors; and correlating blade tip and circumscribing ring segment radial clearance gap relative to angular rotational position of said first blade, with the displacement and rotational data sets, at plural angular positions along the blade tip sweep, in a data analyzer system that is coupled to the data acquisition system.

2. The method of claim 1 further comprising: directly coupling an optical camera having a field of view to one of a plurality of operational turbine blade airfoils; and capturing images within the turbine with the camera during rotor rotation.

3. The method of claim 1, the non-contact displacement sensor comprising a visible light or infra-red probe having at least one photonic energy transmitter and a corresponding receiver.

4. The method of claim 1, the non-contact displacement sensor comprising a pair of tandem visible light or infra-red proximity sensors respectively oriented proximal the blade tip leading and trailing edges.

5. The method of claim 1, the non-contact displacement sensor comprising an ultrasonic proximity sensor.

6. The method of claim 1, the rotor rotational position sensor comprising a tilt sensor, or a triangulated GPS position sensor.

7. The method of claim 1, further comprising coupling the data acquisition and data analyzer systems by wireless communication, cable or by physical transfer of a non-volatile data storage device.

8. The method of claim 1, further comprising coupling one or more of the displacement sensor, the rotational position sensor or the data acquisition system to the turbine blade airfoil with a magnet.

9. A method for measuring gas turbine blade tip and turbine ring segment radial clearance gap, comprising:

providing a gas turbine including: a turbine casing having an access port and an inner circumferential ring segment that fully circumscribes a rotatable rotor oriented within the casing, the rotor having a row of turbine blades radially aligned with the ring segment, each blade having an airfoil that defines an airfoil outer surface and a radially outwardly projecting tip in opposed, spaced relationship with the circumscribing ring segment, each respective blade tip defining a gap between itself and the circumscribing ring segment at a plurality of rotational angular positions of the blade and rotor;

inserting into the turbine casing through the access port, and coupling on an airfoil surface of a first one of said blades at least one non-contact displacement sensor that generates a displacement data set of distance between the displacement sensor and the ring segment;

inserting into the turbine casing through the access port, and coupling on the airfoil surface of the same first one of said blades a rotor rotational position sensor that generates a rotational position data set indicative of rotational angular orientation of said first blade relative to the circumscribing ring segment;

rotating the rotor so that the blade tip of said first blade sweeps at least a portion of the circumscribing ring segment, while generating the displacement data set with the displacement sensor and a rotational position data set with the rotor rotational position sensor at plural angular positions along the blade tip sweep;

acquiring the displacement and rotational position data sets with a data acquisition system that is coupled to the displacement and rotational position sensors; and correlating blade tip and circumscribing ring segment radial clearance gap relative to angular rotational position of said first blade, with the displacement and rotational data sets, at plural angular positions along the blade tip sweep, in a data analyzer system that is coupled to the data acquisition system.

10. The method of claim 9, further comprising: directly coupling an optical camera having a field of view to one of a plurality of turbine blade airfoils; and capturing images within the turbine, including the circumscribing turbine casing, with the camera during rotor rotation.

11. The method of claim 9, further comprising coupling the data acquisition system to one or more turbine blades.

12. The method of claim 11, further comprising coupling the displacement sensor, rotational position sensor and data acquisition system to a common substrate that is in turn coupled to the same airfoil surface.

13. The method of claim 12, the rotational position sensor comprising a tilt sensor, and further comprising coupling the common substrate to the same airfoil surface with a magnet.

14. The method of claim 9, the displacement sensor comprising any one of an infra-red or a visible light probe having at least one photonic energy transmitter and a corresponding receiver, or an ultrasonic proximity sensor.

15. The method of claim 9, further comprising inserting into the turbine casing through the access port and directly coupling an optical camera having a field of view to one of a plurality of turbine blade airfoils, and capturing images within the turbine, including the circumscribing turbine casing, with the camera during rotor rotation.

16. The method of claim 9, the non-contact displacement sensor comprising a pair of tandem non-contact displacement sensors respectively oriented proximal leading and trailing edges of the blade tip of said first one of said blades.

17. The method of claim 9, the rotational position sensor comprising any one of a tilt sensor, or a triangulated GPS position sensor.

18. The method of claim 9, the data acquisition and data analyzer systems communicatively coupled by wireless communication, cable or by physical transfer of a non-volatile data storage device.

19. A method for measuring gas turbine blade tip and turbine ring segment radial clearance gap, comprising:

providing a gas turbine including: a turbine casing having an access port and an inner circumferential ring segment that fully circumscribes a rotatable rotor oriented within the casing, the rotor having a row of turbine blades radially aligned with the ring segment, each blade having an airfoil that defines an airfoil outer surface and a radially outwardly projecting tip in opposed, spaced relationship with the circumscribing ring segment, each respective blade tip defining a gap between itself and the circumscribing ring segment at a plurality of rotational angular positions of the blade and rotor;

inserting into the turbine casing through the access port, and coupling on an airfoil surface of a first one of said blades at least one infra-red displacement sensor that generates a displacement data set of distance between the displacement sensor and the ring segment;

inserting into the turbine casing through the access port, and coupling on the airfoil surface of the same first one of said blades a tilt sensor that generates a rotational position data set indicative of rotational angular orientation of said first blade relative to the circumscribing ring segment;

rotating the rotor so that the blade tip of said first blade sweeps at least a portion of the circumscribing ring segment, while generating the displacement data set with the infra-red displacement sensor and a rotational position data set with the tilt sensor, at plural angular positions along the blade tip sweep;

acquiring the displacement and rotational position data sets, generated at said plural angular positions, with a data acquisition system that is coupled to the infra-red displacement sensor and the tilt sensor; and correlating blade tip and circumscribing turbine casing radial clearance gap relative to angular rotational position of said first blade, with the displacement and rotational data sets, at plural angular positions along the blade tip sweep, in a data analyzer system that is coupled to the data acquisition system.

\* \* \* \* \*